(12) United States Patent
Frisén

(10) Patent No.: US 8,061,839 B2
(45) Date of Patent: Nov. 22, 2011

(54) DEVICE AND METHOD FOR VISION TEST

(75) Inventor: Lars Frisén, Göteborg (SE)

(73) Assignee: Visumetrics AB, Vastra Frolunda (SE)

( * ) Notice: Subject to any disclaimer, the term of this patent is extended or adjusted under 35 U.S.C. 154(b) by 65 days.

(21) Appl. No.: 12/308,226

(22) PCT Filed: Jun. 16, 2007

(86) PCT No.: PCT/EP2007/005322
§ 371 (c)(1),
(2), (4) Date: Dec. 10, 2008

(87) PCT Pub. No.: WO2008/000364
PCT Pub. Date: Jan. 3, 2008

(65) Prior Publication Data
US 2009/0153803 A1   Jun. 18, 2009

(30) Foreign Application Priority Data
Jun. 30, 2006   (EP) .................................... 06116372

(51) Int. Cl.
*A61B 3/08* (2006.01)
*A61B 3/10* (2006.01)
*A61B 3/02* (2006.01)
(52) U.S. Cl. ......... 351/202; 351/205; 351/221; 351/243
(58) Field of Classification Search .................. 351/202, 351/200, 201, 205, 211, 221, 246, 237, 239, 351/243
See application file for complete search history.

(56) References Cited

U.S. PATENT DOCUMENTS

| | | | |
|---|---|---|---|
| 5,640,220 A | 6/1997 | Vo et al. | |
| 5,946,075 A | 8/1999 | Horn | |
| 6,045,515 A | 4/2000 | Lawton | |
| 6,890,077 B2 * | 5/2005 | Dunn | 351/224 |
| 7,235,779 B1 * | 6/2007 | Pinkus et al. | 250/252.1 |
| 7,697,212 B2 * | 4/2010 | Jethmalani et al. | 359/652 |
| 2003/0002014 A1 | 1/2003 | Grant | |
| 2003/0028115 A1 | 2/2003 | Thomas | |
| 2003/0053026 A1 | 3/2003 | Roorda | |
| 2003/0081176 A1 | 5/2003 | Stewart | |
| 2003/0199858 A1 * | 10/2003 | Schelonka | 606/5 |
| 2004/0193070 A1 | 9/2004 | Schilder et al. | |
| 2005/0024585 A1 * | 2/2005 | Dai | 351/205 |
| 2006/0007397 A1 * | 1/2006 | Lai | 351/246 |
| 2006/0028545 A1 * | 2/2006 | Stapleton | 348/62 |
| 2009/0153796 A1 * | 6/2009 | Rabner | 351/201 |

* cited by examiner

*Primary Examiner* — Mohammed Hasan
(74) *Attorney, Agent, or Firm* — Harness, Dickey & Pierce, P.L.C.

(57) ABSTRACT

A device for vision testing comprises a viewing position (6) and an image surface (5). The distance between the viewing position (6) and the image surface (5) is enclosed. The relation between the resolution of the image surface and the distance between the viewing position (6) and the image surface (5) is such that the angle of a point on the image surface (5) is less than or equal to 1 minute of arc seen from the viewing position (6).

21 Claims, 3 Drawing Sheets

DEVICE AND METHOD FOR VISION TEST

FIELD OF INVENTION

The invention relates to a device and a method for vision testing, comprising a viewing position and an image surface, the distance between the viewing position and the image surface being enclosed.

BACKGROUND ART

Testing of the central vision ("in the line of sight") is necessary for diagnosing and following up a wide spectrum of disorders which either destroy, disturb, or disconnect the neural units that make up the visual system. Examples of such disorders include inflammations and degenerations in the macula of the retina, inflammations in the visual nerve, such as multiple sclerosis, and tumour formations pressing against, for instance, the optic nerve or optic chiasm, such as pituitary tumours. In the following the need for improved diagnostics will be developed in more detail using a common disorder as an example.

There is a rapidly increasing number of individuals all over the world with double-sided visual loss due to degeneration of the macula of the eye, referred to as Age Related Macular Degeneration, ARMD. ARMD is the leading cause of blindness in elderly people. Many people know or will soon know somebody suffering from ARMD. ARMD causes an accelerating degradation of visual acuity. ARMD causes in the final stage a serious handicap in everyday life. For instance, the possibilities of reading, watching TV and driving a car are eliminated.

Great efforts are made throughout the world to understand the development of ARMD and to an effective treatment. Promising forms of treatment have just appeared and the search for new drugs is very intense. For optimal results, the treatment must be given at an early stage. It is thus necessary to detect ARMD at an early stage. An early diagnosis and meaningful measurement are key issues in research on and treatment of ARMD.

The most commonly applied test is the classic visual acuity chart that was created around 1850. A patient in the final phase of ARMD has to hold the chart at a reading distance to be able to see the largest letters. The visual acuity chart is an excellent tool when testing spectacles but suffers from great drawbacks when diagnosing and measuring nerve and retinal disorders, including ARMD.

It is established that normal visual acuity can be upheld even with 50% loss of neural units. The problem with visual acuity charts and other similar tests is that the letters contain an excess of information. The test letters can be recognized even if some parts of the letters are invisible. In addition, natural unconscious eye movements assist in filling in the missing parts of the letters, thus making diagnosis of ARMD still more difficult.

The dividing line between central vision (in the line of sight) and peripheral vision (field of vision) is traditionally placed at about 3°, which is at the outer edge of the macula of the retina. Of course, the limit is artificial: vision is "seamless" over the entire field of vision.

Completely different types of tests are used for central and peripheral vision. This is due to the fact that it is difficult to determine what is seen in peripheral vision. For example, it is difficult to read letters that are presented outside about 3° C. The predominant peripheral technique, perimetri, is based on light spots projected in predetermined positions on the inside of a grey hemisphere. The test aims at finding the faintest contrast that can be discovered at each test point (typically about 50 test points). Contrast sensitivity is bracketed with repeated presentations in one and the same position. The predominant test in central vision is visual acuity. As mentioned above, in most cases letter charts are used and here, too, a function level is bracketed by using different letter sizes.

All conventional peripheral and central tests thus use forking techniques in order to specify a function level. The observed function levels can then be compared with normal data. Normal data are widely spread, as are most human characteristics.

SUMMARY OF THE INVENTION

Example embodiments are directed to a device and a method which can be used to diagnose at an early stage disorders affecting the neural units in an eye.

The inventive device and method comprise a viewing position and an image surface, the distance between the viewing position and the image surface being enclosed. Moreover, the relation between the resolution of the image surface and the distance between the viewing position and the image surface is such that the angle of a point on the image surface is less than or equal to 0.5 minutes of arc seen from the viewing position. The image surface is connected to a computer and the computer controls illumination of at least one point on the image surface, which is turned off after a short while. The inventive concept is based on presenting light spots with a smaller diameter than the neural units of the visual system. By a neural unit is meant a "receptive field", which is not the same as light receptors (cones and rods). The light receptors vary in size only to a small extent over the surface of the retina. In general it is difficult to predict the function level based on knowledge of receptor density. This is due to the fact that the receptors "converge" on the next unit in the neuron chain, the ganglion cells, to different extents in different parts of the retina. The convergence is near 1 only in the centre of the macula, the fovea, and rises quickly with increasing eccentricity. As a matter of fact, it is the density of ganglion cells that determines the resolving power. To avoid switching between receptor and ganglion cell terms, the expression neural units will be used in the following. Furthermore, the term "point" is used throughout the text. This term should be interpreted to be equivalent to, for example, image surface elements, matrix elements and pixels.

By presenting light spots with a smaller diameter than the neural units of the visual system, the unexpected side effect occurs that it will not be possible to return to exactly the same test position. In fact the eye oscillates with an amplitude that exceeds the visual angle of the smallest neural units. It is thus not possible to grade the function level in one and the same neural unit. The test principle is instead only to question whether function is present or not in ever-new neural units. This may appear as a drawback but in fact brings a plurality of advantages such as

- The normal limits will be narrow since normally it should be possible for the eye to detect all luminous points.
- A direct connection to the status of the visual system in the diseased eye is obtained. The ratio of "holes" to places in the matrix of neural elements is calculated. There is currently no other vision testing method that has this direct connection.
- The source of error caused by the oscillations of the eye during traditional tests is eliminated by the short exposure time.

It is possible to perform testing using points of any size, but with points larger than the receptor diameter, it is not possible to detect loss of individual neural units. 0.5 minutes of arc is a theoretical ideal. In comparison, the most difficult line on the standard acuity chart corresponds to 1 minute of arc. However, the visual acuity is usually significantly better (up to 0.5 minutes of arc; the normal average is about 0.8 minutes of arc). The ordinary visual acuity chart thus does not allow diagnosis of early loss of visual acuity. Correspondingly, the new testing principle can use points larger than 0.5 minutes of arc but then does not allow detection of disease at an early stage.

Preferably the device comprises a tube. The image surface is arranged at one end of the tube, which means that the other end of the tube is adapted to be the viewing position. A simple optical system is preferably placed in the viewing position to guarantee that the image surface is in the focus of the viewer. Most preferably, the length of the tube is less than 30 cm. This has the advantage that a vision test with the inventive device is relatively easy to arrange. The ease of arrangement is that the device can be placed at will, that is, a large and lightproof room is not required: the tube replaces the room.

A tube makes it possible to use an SLM (Spatial Light Modulator) as an image surface. There are three main types: transmissive and reflective liquid crystal matrices and reflective micro mirrors (DLP=Digital Light Projection), which are normally used for example in digital projectors. Common examples are LCD matrices (Liquid Crystal Display) and DLP matrices in combination with an external light source, for instance a light bulb or an LED (Light Emitting Diode). It is advantageous to use a laser since the matrix can pass very thin, collimated beams which due to their small cross-sectional areas are very little affected by any defects in the optics of the eye. The width of each matrix is typically about 10-20 mm. Preferably the width is less than 30 mm. The most common number of elements is 1024×768 (XVGA in PC terminology). Thus such an element typically has the size of 25 μm×25 μm. The device and the method according to the invention require luminous points with a maximum width less than or equal to 0.5 minutes of arc, and most preferably about 0.5 minutes of arc. This is achieved with the above-mentioned size of element at a viewing distance of about 0.2 m. An SLM can relatively easily be controlled by an ordinary PC.

Preferably the matrix/image surface is such that the points can be lighted with optional colours. This has the advantage that several functions of the eye can be checked.

It is also advantageous to have a device as described above with adjustable luminance. Points of any luminance can be shown. If the luminance is low, it will be difficult or impossible to see the points. If the luminance is very high, it may destroy the retina (cf. for example photocoagulation treatment of diabetes). Furthermore the size of the retinal image is determined by the luminance (cf. the apparent sizes of faint and bright stars in the night sky: the sizes are experienced differently although all stars are mathematically punctiform). The optimal luminance is currently unknown. There is much to indicate that the level should be in the vicinity of the luminance of a "common visual acuity chart", that is 200-300 candela/m$^2$. It must be possible to set the luminance at the desired level, that is, the device must contain a calibrating mechanism. Such a mechanism may consist of a sensor in the beam path, with readable output, and a possibility of controlling the luminance (for example in software, or with neutral filters).

BRIEF DESCRIPTION OF THE DRAWINGS

The invention will in the following be described in more detail by way of embodiments with reference to the accompanying drawings.

DESCRIPTION OF PREFERRED EMBODIMENTS

Figure 1:
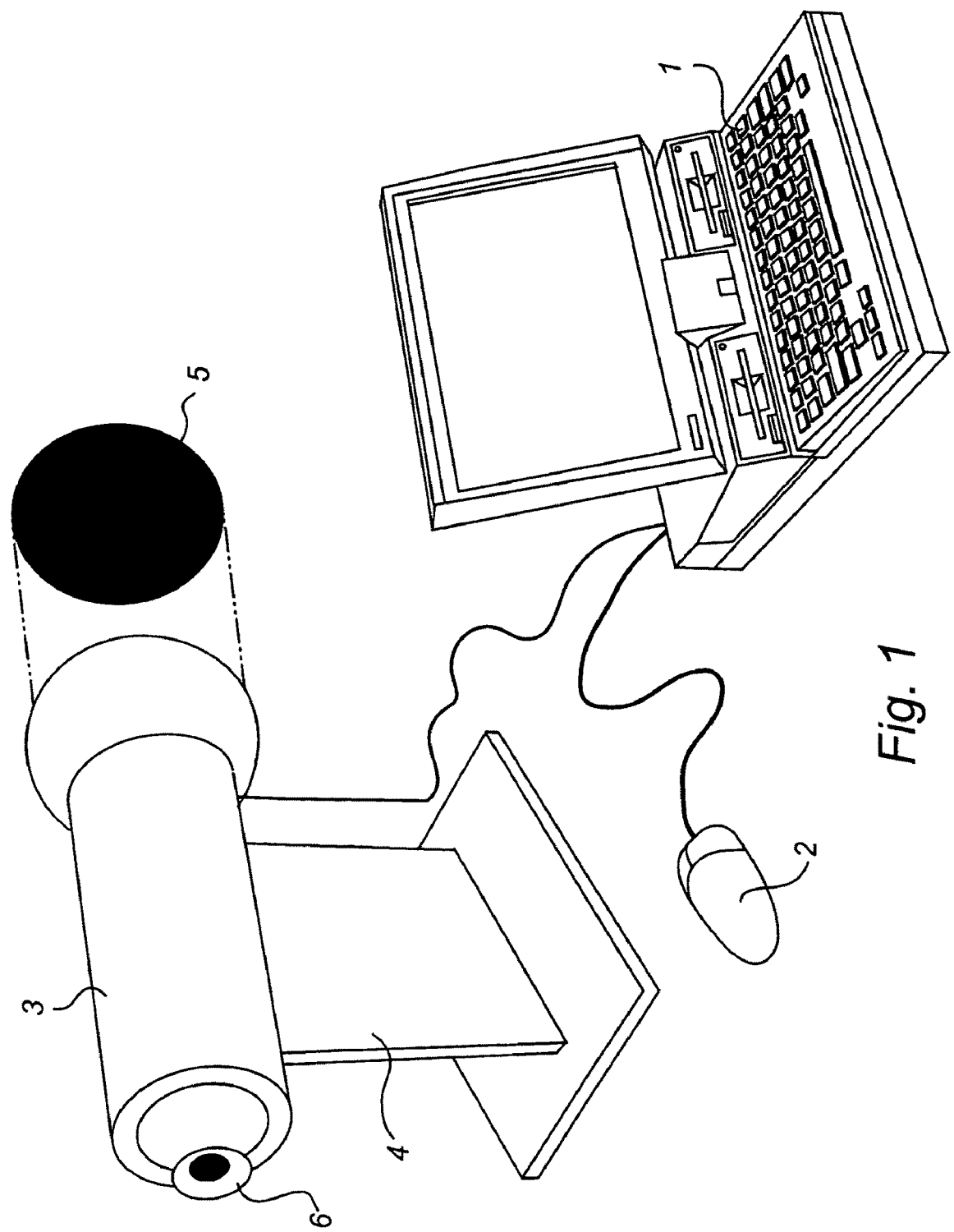
FIG. 1 is a perspective view of a vision testing assembly according to an embodiment of the present invention.

FIG. 1 shows a vision testing assembly according to an embodiment of the present invention involving a PC 1, including a mouse 2, and a tube 3 on a stand 4. For easy understanding, an example of an image surface 5 with two lighted points is shown extracted from the tube 3. An eye 6 is illustrated in the viewing position.

Figure 2:
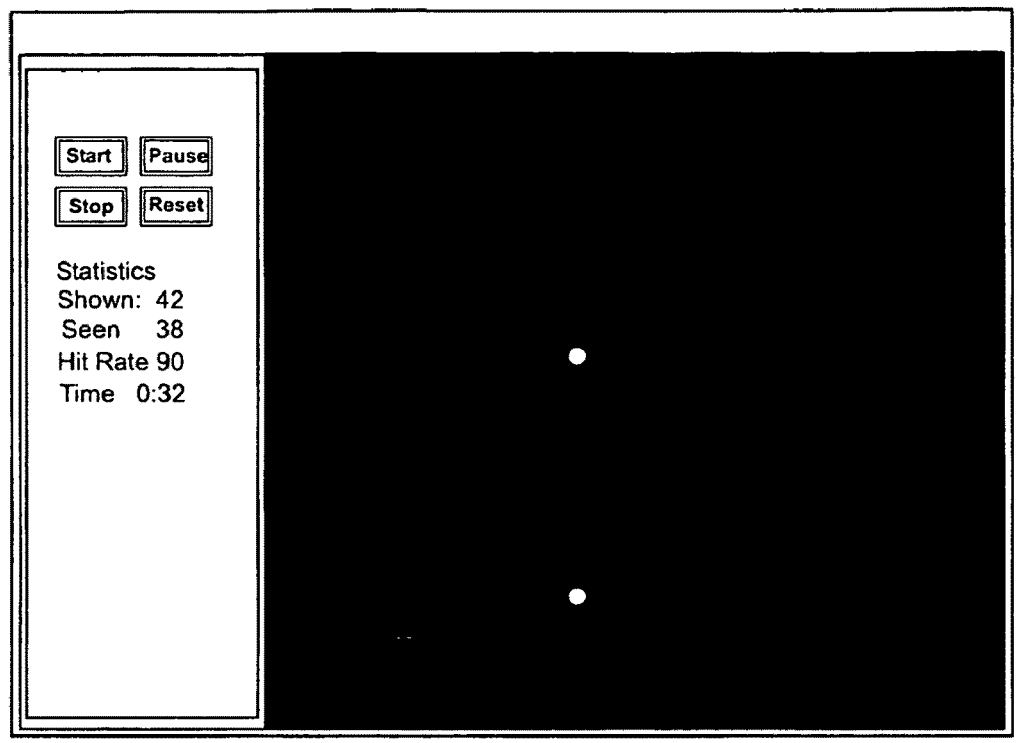
FIG. 2 shows an example of a display image during testing.
Figure 3A:
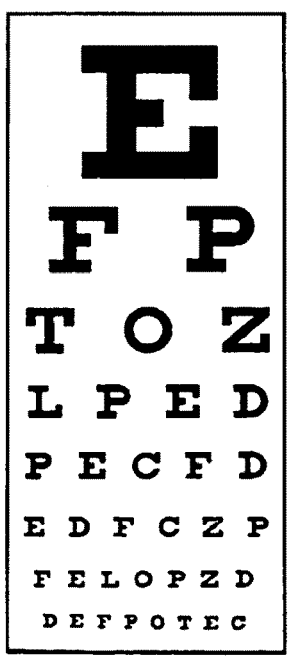
FIGS. 3a-3d illustrate simulation of loss of vision due to ARMD with a visual acuity chart.
Figure 3B:
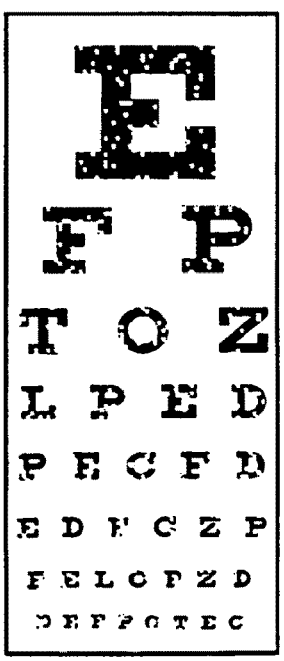
Figure 3C:
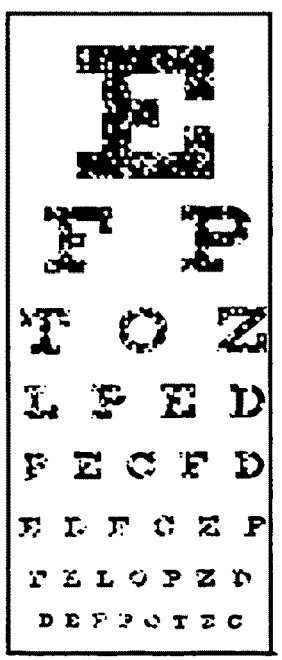
Figure 3D:
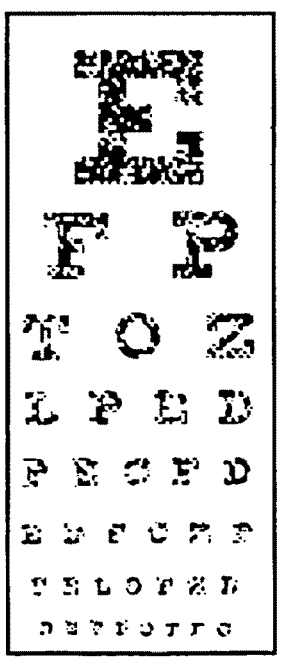
Figure 4A:
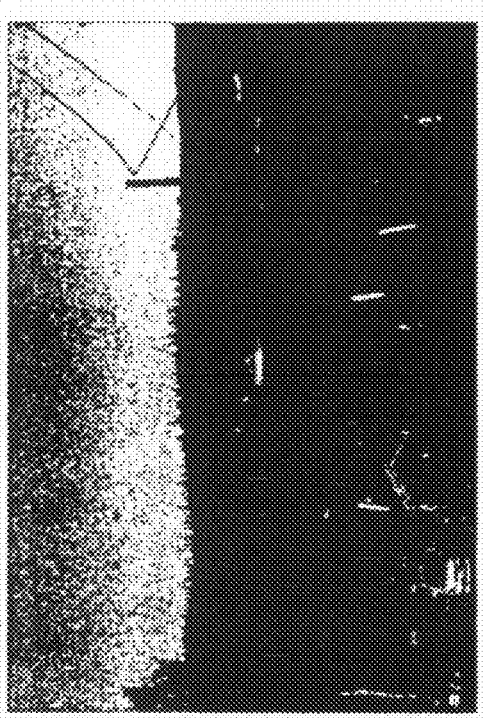
FIGS. 4a-4d schematically illustrate the development of ARMD symptoms.
Figure 4B:
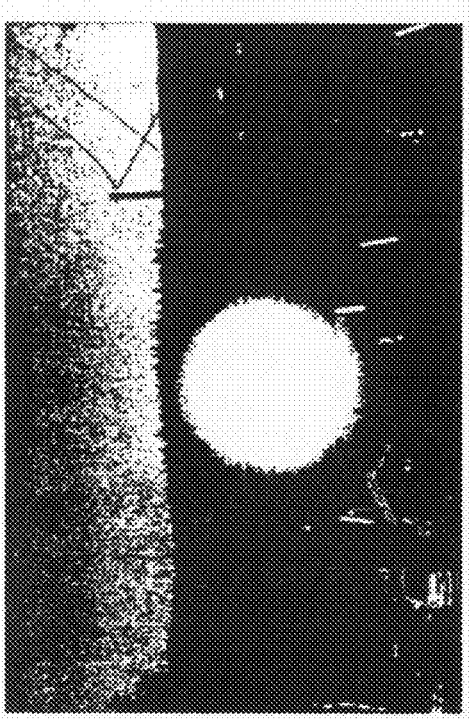
Figure 4C:
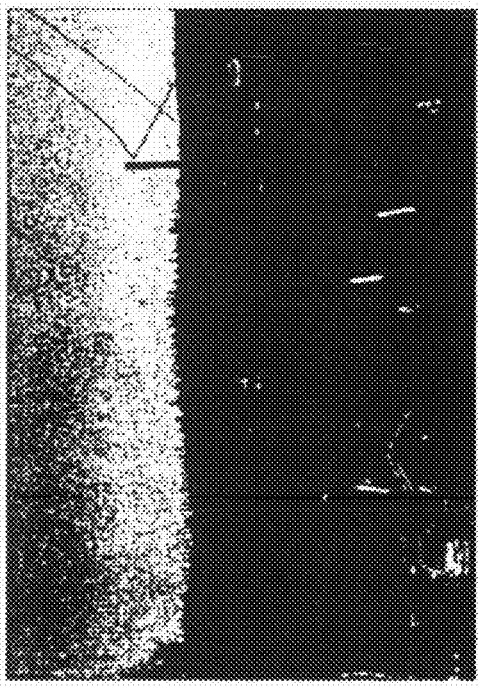
Figure 4D:
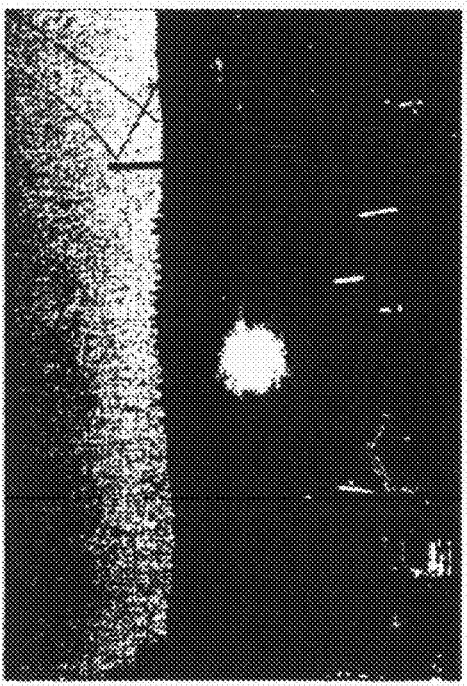

FIG. 2 shows an example of the display image of the computer during testing. A vision test according to the present invention can be carried out in various ways. One way is to randomly and briefly light one or two points on the image surface and after that briefly light new sets of one or two other points. This is repeated until a sufficient number of points on the image surface have been lighted. The time during which a certain point is lighted should be less than 0.2 s, which is the latency of actively searching eye movements. Parallel to the above-described process, a viewer/patient registers by clicking the mouse how many points he has observed. By lighting more than one point at a time, the test can be performed more quickly. All points on the image surface need not be lighted since statistical analysis makes it possible to estimate the degree of loss of vision, if any, also in tests using a smaller number of points.

FIG. 2 also shows an example of results in a test where the number of points shown and also the number of points observed are presented. In the example, the number of points shown is 42 and the number of points observed is 38, which equals a hit rate of about 90%. This thus indicates a loss of vision of 10%. Prior art technique requires a loss of vision of about 50% for a disease to be detected. With the present invention it is consequently possible to intervene at a significantly earlier stage in order to arrest the process. In FIGS. 3a-3d, different degrees of loss of vision due to loss of neural units have been simulated on a visual acuity chart in the absence of eye movements. The degree of loss in FIGS. 3a-3d is 0%, 10%, 20% and 30%, respectively. It will thus be appreciated that in the presence of eye movements it would not be possible to detect a loss of 30% by means of a visual acuity chart.

FIGS. 4a-4d illustrate schematically the development of ARMD. The "focus" is in this case turned to the centre of the image.

It will be appreciated that many modifications of the above-described embodiments of the invention are conceivable within the scope of the invention as defined by the appended claims.

For example, ARMD has been used as an example of a disease that can be detected using the present invention for pedagogical purposes in order to simplify understanding. It is thus possible to use the invention also to detect a number of other diseases that affect the neural units of an eye.

The invention claimed is:

1. A device for vision testing, comprising a viewing position and an image surface, a distance between the viewing position and the image surface being enclosed, wherein a ratio of a resolution of the image surface to a-the distance between the viewing position and the image surface is such that an angle of at least one point on the image surface is less than or equal to 0.5 minutes of arc seen from the viewing position, the at least one point on the image surface is randomly illuminated, and an observation of the randomly illuminated at least one point is registered by a viewer.

2. The device as claimed in claim 1, further comprising:
a tube, the image surface being at one end of the tube and the viewing position being at the other end of the tube.

3. The device as claimed in claim 2, wherein the viewing position includes optics.

4. The device as claimed in claim 2, wherein the tube is shorter than 30 cm.

5. The device as claimed in claim 4, wherein a width and a height of the image surface are less than 30 mm.

6. The device as claimed in claim 1. wherein a color of the at least one point on the image surface is adjusted.

7. The device as claimed in claim 1, wherein a luminance of the at least one point on the image surface is adjusted.

8. A system, comprising:
the device of claim 1; and a computer configured to receive an input from the viewer indicating the observation of the at least one point illuminated on the image surface when viewed from the viewing position.

9. The system as claimed in claim 8, wherein
the device is further configured to illuminate on the image surface a plurality of new sets including at least one other point after illuminating the at least one point, and
the computer is further configured to receive an input from the viewer indicating an observation of the least one other point in the new sets when viewed from the viewing position, and to determine a loss of vision of the viewer by calculating a ratio of a number of points registered by the viewer and a number of points illuminated on the image surface.

10. The device of claim 1, wherein the illuminated at least one point has a diameter smaller than a neural unit of an eye.

11. A method for vision testing, comprising:
arranging a viewing position and arranging an image surface at a distance from one another so that a relation between a resolution of the image surface and the distance is such that an angle of at least one point on the image surface is less than or equal to 0.5 minutes of arc seen from the viewing position;
connecting a computer to the image surface and randomly illuminating the at least one point on the image surface using the computer;
registering, by a viewer, an observation of the at least one point illuminated on the image surface; and
after a period of time, turning off said at least one point illuminated on the image surface.

12. The method as claimed in claim 11, in which the period of time is shorter than 0.2 s.

13. The method as claimed in claim 12, further comprising:
illuminating at least one other point different from the at least one point after the period of time.

14. The method as claimed in claim 11, wherein the viewer registers the observation of the illuminated at least one point on the same computer that controls the illumination of said at least one point.

15. The method as claimed in claim 11, further comprising:
illuminating at least one other point on the image surface after turning off said at least one point.

16. The method as claimed in claim 11, wherein at least two points are illuminated.

17. The method as claimed in claim 16, wherein the viewer registers a number of observed points.

18. The method as claimed in claim 11, wherein the at least one point on the image surface is illuminated in color.

19. The method as claimed in claim 11, wherein a luminance of the at least one point on the image surface is adjusted.

20. The method as claimed in claim 11, further comprising:
illuminating the at least one point having a diameter smaller than a neural unit of an eye.

21. The method as claimed in claim 11, further comprising:
illuminating at least one other point on the image surface after turning off the at least one point; registering, by the viewer, an observation of the at least one other point illuminated on the image surface; and determining a loss of vision of the viewer by calculating a ratio of a number of points registered by the viewer and a number of points illuminated on the image surface.

* * * * *